US012788909B2

(12) United States Patent
Baek et al.

(10) Patent No.: US 12,788,909 B2
(45) Date of Patent: Nov. 10, 2026

(54) COMPACT TELESCOPING SPACER WITH DOUBLE-BARREL FOR METERED DOSE INHALER

(71) Applicant: Blue Ocean Group, LLC, Irvine, CA (US)

(72) Inventors: Simon Baek, Irvine, CA (US); Cindy Baek, Irvine, CA (US); Henry Hsu, Aliso Viejo, CA (US)

( * ) Notice: Subject to any disclaimer, the term of this patent is extended or adjusted under 35 U.S.C. 154(b) by 482 days.

(21) Appl. No.: 18/479,137

(22) Filed: Oct. 2, 2023

(65) Prior Publication Data

US 2024/0108830 A1 Apr. 4, 2024

Related U.S. Application Data

(60) Provisional application No. 63/378,299, filed on Oct. 4, 2022.

(51) Int. Cl.
*A61M 15/00* (2006.01)

(52) U.S. Cl.
CPC .... *A61M 15/0086* (2013.01); *A61M 15/0016* (2014.02); *A61M 15/0021* (2014.02)

(58) Field of Classification Search
CPC .......... A61M 15/0086; A61M 15/0016; A61M 15/0021; A61M 15/0015; A61M 2202/203; A61M 2202/206; A61M 2205/0205; A61M 15/0025; A61M 15/0088; A61M 15/009; A61M 2205/0238
See application file for complete search history.

(56) References Cited

U.S. PATENT DOCUMENTS

| | | | | |
|---|---|---|---|---|
| 5,746,197 A | 5/1998 | Williams | | |
| 6,595,206 B2 * | 7/2003 | Vito | B05B 15/656 | 128/200.23 |
| 7,832,393 B2 * | 11/2010 | Vito | A61M 15/0086 | 128/200.23 |
| 10,792,446 B1 | 10/2020 | Baek | | |

(Continued)

FOREIGN PATENT DOCUMENTS

GB 2491178 A * 11/2012 ........ A61M 15/0088

OTHER PUBLICATIONS

Search Report by the USPTO dated Feb. 15, 2024 for application PCT/US23/75676.

(Continued)

*Primary Examiner* — Victoria Murphy
(74) *Attorney, Agent, or Firm* — AGK Patent & Trademark Law; Philip Y Kim

(57) ABSTRACT

A spacer device for use with a metered dose inhaler (MDI). The spacer device comprises an aerosol chamber for holding the aerosolized medication sprayed from the MDI. The aerosol chamber comprises a fixed barrel and a sliding barrel. The sliding barrel is in telescoping engagement with the fixed barrel. The sliding barrel slides within the alleyway between the inner shell and outer shell of the fixed barrel. There is an MDI adapter at the distal end of the aerosol chamber, which receives and secures the MDI to the spacer device. In use, the MDI is secured to the spacer device. The sliding barrel is pulled out of the fixed barrel to enlarge the aerosol chamber. After MDI treatment, the sliding barrel is pushed back into the fixed barrel to put the aerosol chamber in compact configuration.

20 Claims, 11 Drawing Sheets

(56) References Cited

U.S. PATENT DOCUMENTS

| | | | | |
|---|---|---|---|---|
| 11,395,890 | B2 * | 7/2022 | Meyer ............... | A61M 15/0086 |
| 2019/0366018 | A1 * | 12/2019 | Conlon ............. | A61M 15/0021 |

OTHER PUBLICATIONS

Written Opinion by the USPTO dated Feb. 15, 2024 for application PCT/US23/75676.

Patient instructions for "AeroChamber" anti-static valved holding chamber by Monaghan Medical.

Patient instructions for "Space Chamber plus" by Medical Developments International.

* cited by examiner

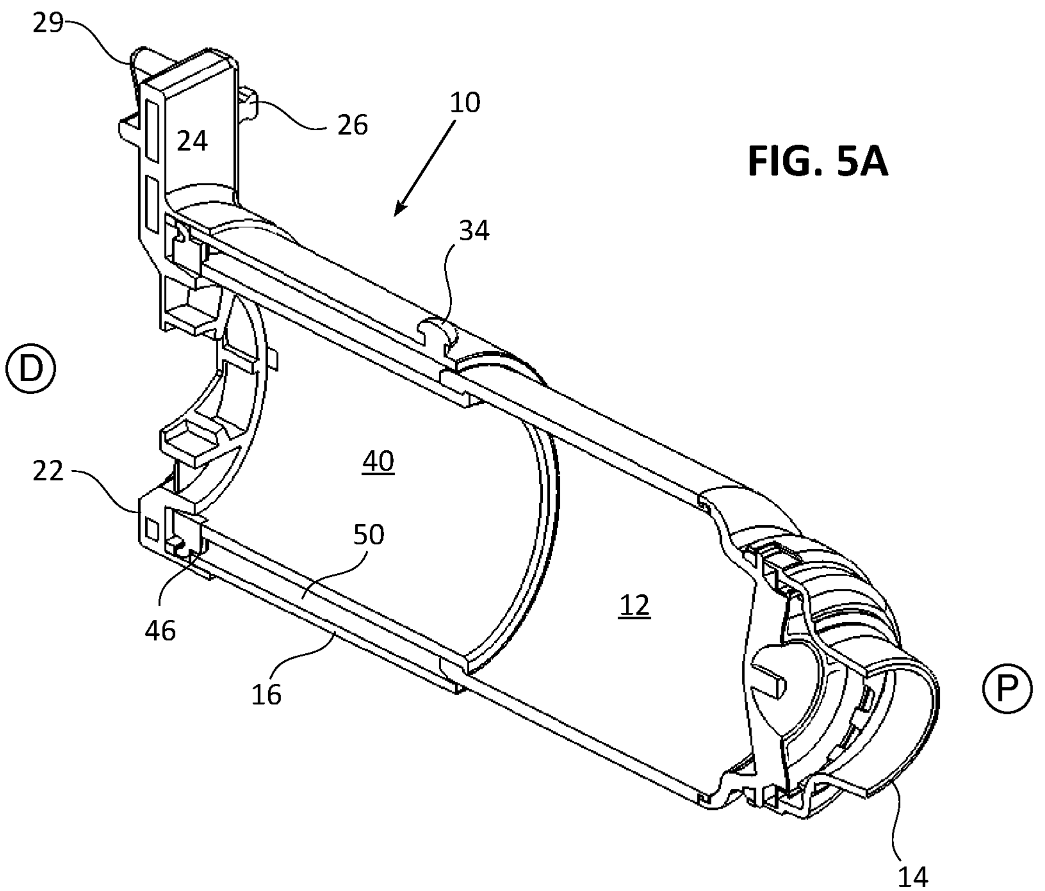
FIG. 5A
FIG. 5B
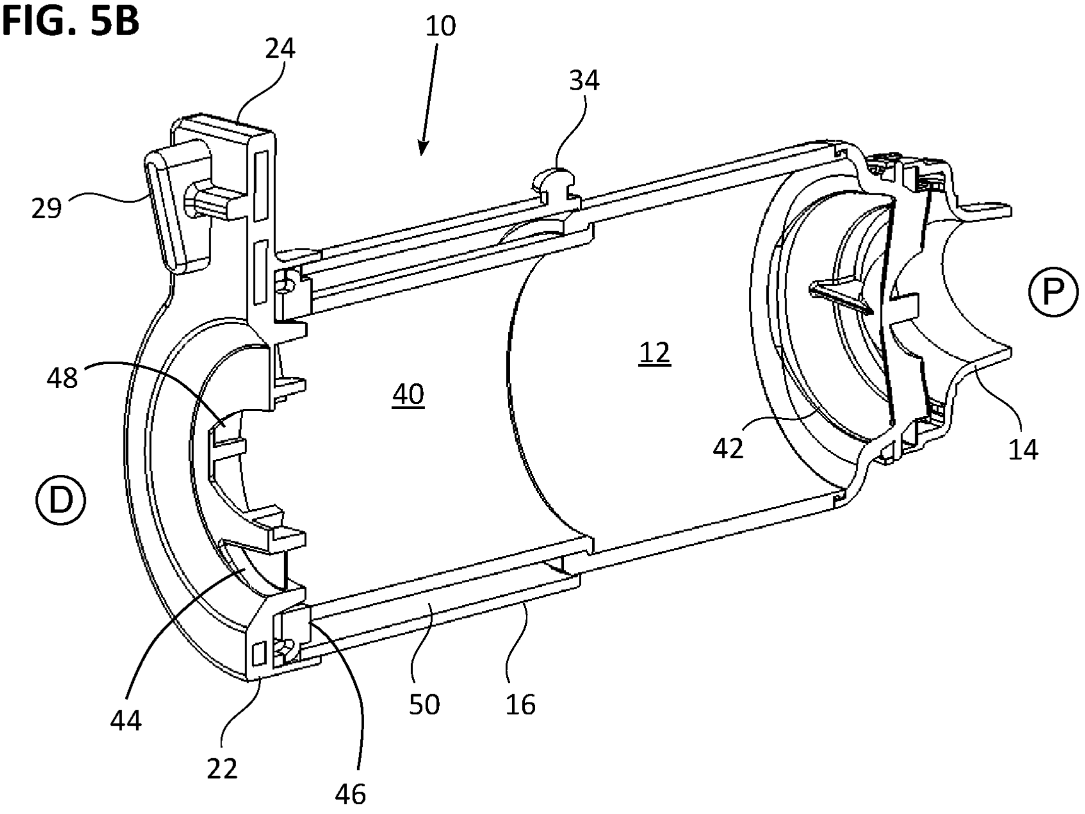

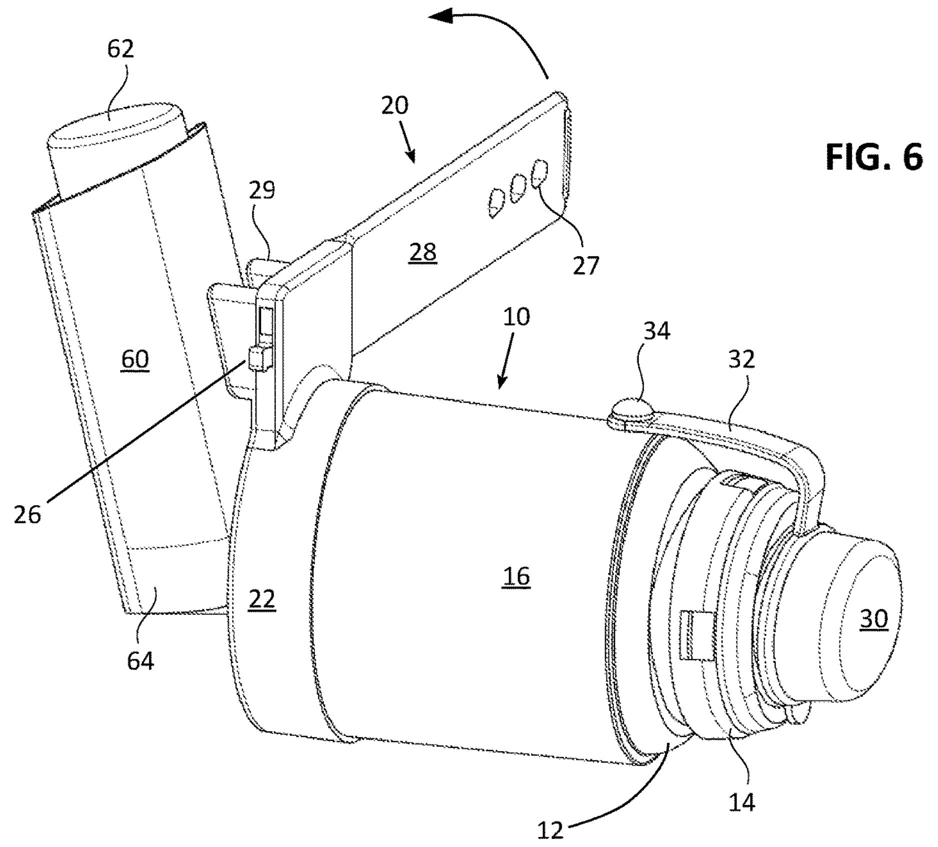
FIG. 6
FIG. 7
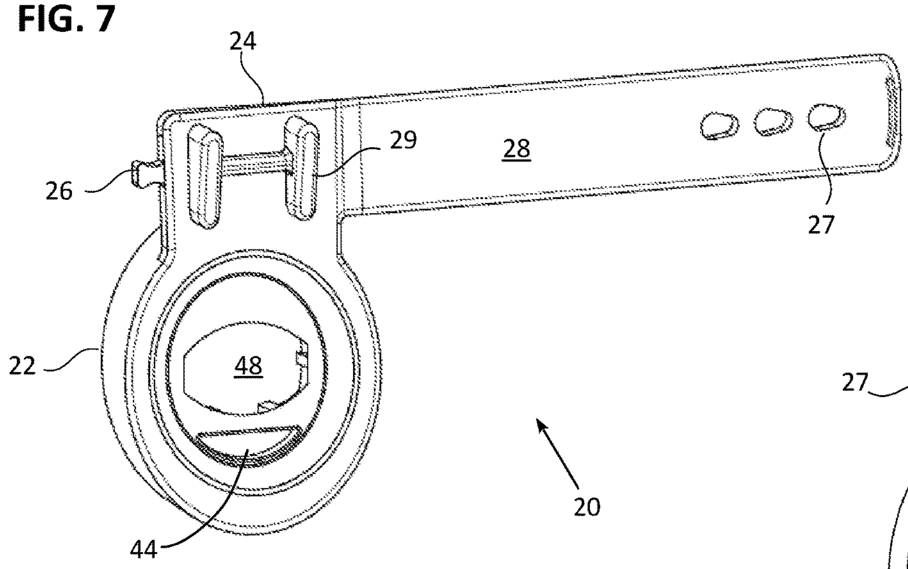
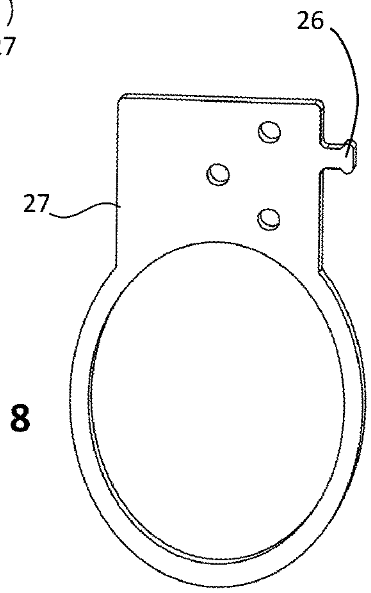
FIG. 8

COMPACT TELESCOPING SPACER WITH DOUBLE-BARREL FOR METERED DOSE INHALER

TECHNICAL FIELD

This invention relates to spacer devices for metered dose inhalers for administering medications.

BACKGROUND

Metered dose inhalers (MDI) are used for administering medications, such as bronchodilator drugs and corticosteroids, to the lungs. FIG. 1 shows an example of a metered dose inhaler 90 and its mechanism of action. The metered dose inhaler 90 comprises a pressurized medication canister 92 and an actuator 99, which holds the canister 92. The actuator 99 comprises a boot portion 94 for holding the canister 92, a spray nozzle 95, and a mouthpiece 96, which is also the outlet for the aerosol spray 98.

The canister 92 holds a reservoir 97 of medication and is pressurized with a propellant. A metering valve 93 is located at the bottom of the canister 92 and the medication flows out through a stem 91. The user loads the canister 92 into the boot portion 94 of the actuator 99 such that the stem 91 fits into the spray nozzle 95. When the user presses down on the canister 92, the valve stem 91 presses into the spray nozzle 95, causing it to discharge a preset amount of medication as an aerosolized spray 98 out of the mouthpiece 96 for delivery into the user's lung. When used properly, the user inhales the aerosolized medication 98 through the mouth and into the bronchial passageways of the lungs.

However, MDIs are not very efficient at drug delivery; they deliver only about 10% of the dose to the lungs, with the rest being deposited elsewhere, such as the oropharynx. This is because pressurized MDIs generate an aerosol spray with a velocity that is faster than the patient can inhale. This puts a lot of demand on the users' performance to synchronize their inhalation with the spray actuation in order to release the aerosol spray at the beginning of inhalation. This problem is particularly acute in children and the elderly. With the lack of proper synchronization, instead of being inhaled into the lung, much of the sprayed medication may be deposited onto the back of the mouth or pharynx. In addition to loss of therapeutic effectiveness, this can cause cough, voice hoarseness, fungal infections, and absorption of the medication into the bloodstream.

Because of these difficulties, many patients are advised to use a spacer that is fitted to the mouthpiece of the MDI to overcome some of the problems of poor coordination and oropharyngeal deposition. Spacers work by lengthening the distance between the actuator mouthpiece and the user's mouth, thus giving the user more time to synchronize inhalation and reducing the impaction onto the oropharynx. Also, evaporation of spray solvent would decrease the size of particles, facilitating more deposition in the lungs and better penetration to peripheral airways.

FIG. 2 shows an example of a conventional spacer device 54 of the prior art. The spacer 54 comprises a barrel-shaped chamber 56, a mouthpiece 57 at the front, a one-way valve 58, and a socket opening 55 at the back for fitting the inhaler outlet/mouthpiece. In use, the inhaler mouthpiece is fitted into the socket opening 55 at the back of the spacer 54. The user puts their mouth on the mouthpiece 57 at the front the spacer 54. When the user actuates the metered dose inhaler, the aerosol spray is discharged into the chamber 56 and suspended momentarily therein. The user then inhales the aerosolized medication suspended in the chamber 56 by breathing in and out.

The one-way valve 58 allows the user to inhale the medication through the spacer 54. In case the user exhales, the one-way valve 58 would act to divert the exhaled breath outward rather than entering the chamber 56. Some spacers are also equipped with a whistle as a flow rate indicator, i.e. making a whistling sound if the user is inhaling too quickly.

Yet, there are still problems with existing spacers. There is a tradeoff between size and effectiveness. Spacers can have a compact design, but those are too short and small to be effective. More complex spacer designs, such as the valved holding chambers (VHC), have a wider and longer barrel to improve drug delivery effectiveness, but the problem is that they are too bulky, making them inconvenient to carry around. This is a very serious problem for patients who must carry around their MDIs at all times for acute asthma attacks. Because they are so bulky, MDI users often leave their spacers at home instead of carrying it with them. Thus, there is a need for a spacer device that is compact, sanitary, and easy-to-carry, yet large enough for effective drug delivery.

SUMMARY

The present invention provides a compact spacer device for a metered dose inhaler. In one aspect, the present invention is a spacer device for a metered dose inhaler (MDI). The spacer device has a proximal end and a distal end. The proximal/distal designation is made with proximal being towards the user and distal being away from the user. The spacer device may be made as a single unitary structure, or its various segments may be separate parts that are joined together.

Aerosol Chamber: The spacer device comprises an aerosol chamber for holding the aerosolized medication sprayed from the MDI. The aerosol chamber comprises a fixed barrel and a sliding barrel. The fixed barrel is located distal to the sliding barrel. The fixed barrel comprises a double-wall, i.e. two tubular shells that are separated by a narrow gap, i.e. alleyway. The fixed barrel comprises an outer shell and an inner shell which are in coaxial alignment. The outer shell and the inner shell may together form a unitary structure, or they may be separate pieces that are joined together to work cooperatively in the manner described herein.

The sliding barrel is coupled to the fixed barrel by a telescoping arrangement within the alleyway between the outer shell and inner shell of the fixed barrel. Thus, the aerosol chamber is designed such that the sliding barrel can telescope in and out of the fixed barrel. When fully retracted, the sliding barrel is contained inside the alleyway between the outer shell and inner shell. This puts the aerosol chamber (and spacer device) in compact configuration.

In preparation for use, the sliding barrel is pulled out of the fixed barrel. The sliding barrel slides out from the alleyway between the double-walls of the fixed barrel. When the sliding barrel is fully telescoped out, this puts the aerosol chamber (and spacer device) in extended configuration.

The fixed barrel or sliding barrel could be made of a hard plastic material. The fixed barrel or sliding barrel could have any suitable transverse cross-sectional shape, such as circular, oblong, oval, rounded square, etc. (which may be symmetrical or asymmetrical). Both the fixed barrel and sliding barrel may have matching shapes to allow for telescoping alignment.

MDI Adapter: In use, the MDI is attached to the distal end of the spacer device. The spacer device comprises an MDI adapter to mate the MDI to the aerosol chamber (and spacer device). The MDI adapter could have any suitable design to serve that function. The MDI adapter may be made of any suitable material that is softer and more flexible than the fixed barrel or sliding barrel. For example, it could be made of a soft elastomeric plastic material such as silicone or polyurethane.

The MDI adapter has a fastening means for securing the MDI to the spacer device. For example, the fastening means could be a strap that wraps around the MDI and attaches back onto the MDI adapter. This fastening means helps the user in handling the spacer device and MDI as a single unitary assembly. Also, having the MDI coupled to the spacer device with the fastening means gives the user a perception that this combined assembly is intended to work as a single unit (instead of using the MDI separately). That is, it helps educate and remind the user that (in general) the MDI should always be used with a spacer to improve overall medication efficacy. These factors help improve user compliance in properly using the MDI with the spacer device.

In some embodiments, the fastening means comprises a strap mount and an MDI strap extending from the strap mount. In use, the strap is wrapped around the MDI and could be secured by any suitable means. For example, the strap could have holes that hook onto a strap hook on the strap mount. Other examples of fastening means could use components such as anchoring knobs, through-holes for mating, elastic bands, plastic ties, harnesses, latches, hooks, snaps, Velcro (hook-and-loop fastening), etc.

The MDI adapter may have an adaptor ring for attaching to the distal end of the fixed barrel. The MDI adapter has a rear opening for receiving the spray outlet of the MDI. In some embodiments, the MDI adapter comprises a rigid subframe that is more rigid than the main body of the MDI adapter.

Zero Draft Construction: The construction of the fixed barrel or sliding barrel may have some special characteristics. One or more parts of the fixed barrel may be constructed by zero draft molding. To specifically define the structural result of this type of construction, define a point A and point B on the inner shell or the outer shell of the fixed barrel. The distance between the selected points A and B is 3.0 cm. The thickness of the shell (inner or outer) is substantially or essentially the same at both points. That is, the thickness at point B differs from the thickness at point A by an amount that is less than 8% of the thickness at point A.

In some embodiments, the inner shell has zero draft construction whereas the outer shell does not have zero draft construction. That is, the thickness of the outer shell at point A and point B are different (not essentially the same). In some embodiments, both the inner shell and the outer shell have zero draft construction on their inside surfaces, but have draft angles on their outside surfaces. That is, the thickness of both the inner shell and outer shell at point A and point B are different. However, because of the zero draft construction on their inside surfaces, the alleyway therebetween has constant width.

Likewise, the sliding barrel could be constructed by zero draft molding. To specifically define the structural result of this type of construction, define a point A and point B on the sliding barrel. In this case, the thickness of the sliding barrel is substantially or essentially the same at both points. That is, the thickness at point B differs from the thickness at point A by an amount that is less than 8% of the thickness at point A.

The spatial relationship between the fixed barrel and the sliding barrel may have one or more special features. These spatial relationships could be defined by measurement on a longitudinal cross-section side view of the fixed barrel and the sliding barrel, which delineates the walls thereof. In some embodiments, when the sliding barrel is completely retracted into the fixed barrel, the wall of the sliding barrel has an incline angle relative to the inner shell, the outer shell, or both. This incline angle is very small, such as in the range of 0.3 to 3°. Another way of specifying the incline is to measure the difference in the outer gap, which is the width of the gap between the inner surface of the outer shell and the outer surface of the sliding barrel, when the sliding barrel is fully retracted inside the fixed barrel. Referring to the selected points A and B above, where point A is located distal to point B, the outer gap at point A is wider than the outer gap at point B. In some cases, the outer gap at point A is at least 25% wider than the outer gap at point B.

Alleyway: The fixed barrel could be designed such that the width of the alleyway between the outer shell and inner shell has substantially or essentially constant width. For the purpose of defining this constant-width feature of the alleyway, specify a point A and point B on the fixed barrel. The distance between the selected points A and B is 3.0 cm. In some embodiments, the width of the alleyway between the outer shell and inner shell of the fixed barrel is substantially or essentially the same at both points. That is, the width of the alleyway at point B differs from the width at point A by an amount that is less than 8% of the width at point A.

Cushion Bumper: The cushion bumper on the MDI adapter could be specially designed to work with an MDI having an angled shape. For this, the cushion bumper could have an inclined angle so that it can conform to the shape of the MDI. This inclined angle may vary to accommodate the different angles of the various types of MDIs that are available. The elevation of the cushion bumper relative to the strap mount decreases along the direction towards the central longitudinal axis of the spacer device. For the purpose of defining this inclined angle feature of the bumper, specify a point J and point K on the bumper such that point K is located closer to the central longitudinal axis of the spacer device than point J. The distance between the selected points J and K is 0.75 cm. Because of the inclined angle, the elevation of the cushion bumper at point J is higher than the elevation at point K.

Dimensions: There are a range of dimensions suitable for design of the spacer device and its various components. As an example, the full length of the aerosol chamber may be in the range of 3-15 cm in compact configuration and 6-20 cm in extended configuration. As an example, the inner diameter of the fixed barrel or sliding barrel may be in the range of 2-7 cm wide.

Method of Use: In another aspect, the present invention is a method of using an MDI with a spacer device of this invention. The method comprises having an MDI and a spacer device of this invention. The MDI is attached to the spacer device by inserting the spray outlet of the MDI into the rear opening of the MDI adapter. The fastening means of the MDI adapter is used to secure the MDI to the spacer device. In relevant embodiments, the MDI adapter comprises a strap that is wrapped around the MDI to secure the MDI to the spacer device. In relevant embodiments, the strap is hooked onto a strap hook on the MDI adapter.

The sliding barrel is pulled out of the fixed barrel to put the spacer device in extended configuration. In relevant embodiments, the user removes the mouthpiece cap to expose the spacer device mouthpiece. This also frees the sliding barrel from the tether restraint. The user inserts the mouthpiece of the spacer device into their mouth and actuates the MDI. After use, the sliding barrel is pushed back into the fixed barrel to put the spacer device in compact configuration. If relevant, the mouthpiece cap is put back onto the spacer device mouthpiece to cover it and keep the spacer device in compact configuration.

BRIEF DESCRIPTION OF THE DRAWINGS

FIG. 3 shows the spacer device in extended configuration; FIG. 4 shows the spacer device in compact configuration.

FIGS. 5A and 5B show cut-away side views of the spacer device. FIG. 5A shows one perspective view; FIG. 5B shows an alternate perspective view.

FIG. 6 shows the compact spacer device with a metered dose inhaler (MDI) attached thereto.

FIG. 7 shows the back side of the MDI adapter.

FIG. 8 shows a rigid subframe that is inserted within the MDI adapter.

FIG. 13A shows the sliding barrel partially pulled out of the double-wall; FIG. 13B shows the sliding barrel fully inserted into the double-wall; FIG. 13C shows a larger view of the double-wall.

FIG. 14A shows the sliding barrel extended out; FIG. 14B shows a contaminant on the sliding barrel; FIG. 14C shows the sliding barrel inside the double-wall of the fixed barrel; FIG. 14D shows the sliding barrel extended out again.

FIG. 17A shows the aerosol chamber in compact configuration; FIG. 17B shows the sliding barrel partially pulled out of the fixed barrel.

FIG. 18A shows the aerosol chamber in compact configuration; FIG. 18B shows the sliding barrel partially pulled out of the fixed barrel.

DETAILED DESCRIPTION OF EXAMPLE EMBODIMENTS

To assist in understanding the invention, reference is made to the accompanying drawings to show by way of illustration specific embodiments in which the invention may be practiced. The drawings herein are not necessarily made to scale or actual proportions. For example, lengths and widths of the components may be adjusted to accommodate the page size.

Figure 1:
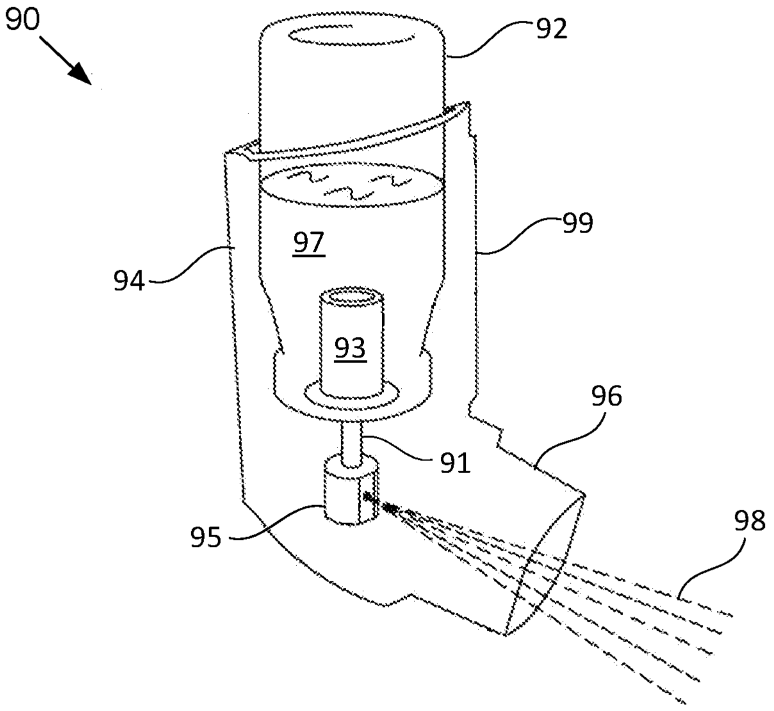
FIG. 1 (prior art)
FIG. 1 shows a perspective view of an example of a metered dose inhaler and its mechanism of action.
Figure 2:
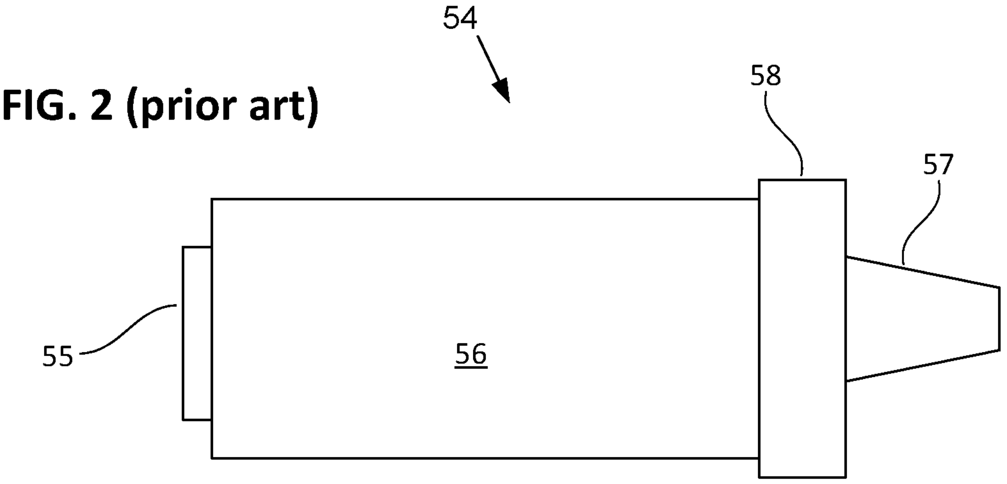
FIG. 2 (prior art)
FIG. 2 shows a side view of a conventional spacer device of the prior art.
Figure 3:
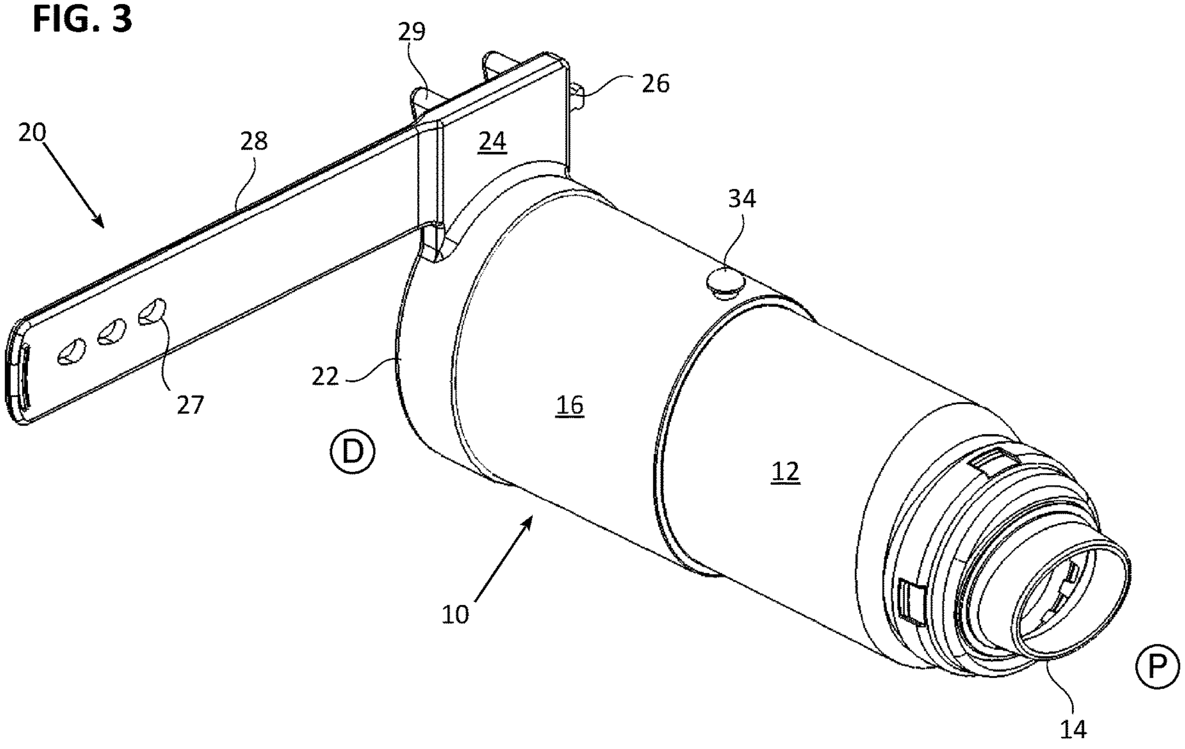
FIGS. 3 and 4 show perspective views of an example of a compact spacer device of the present invention.
Figure 4:
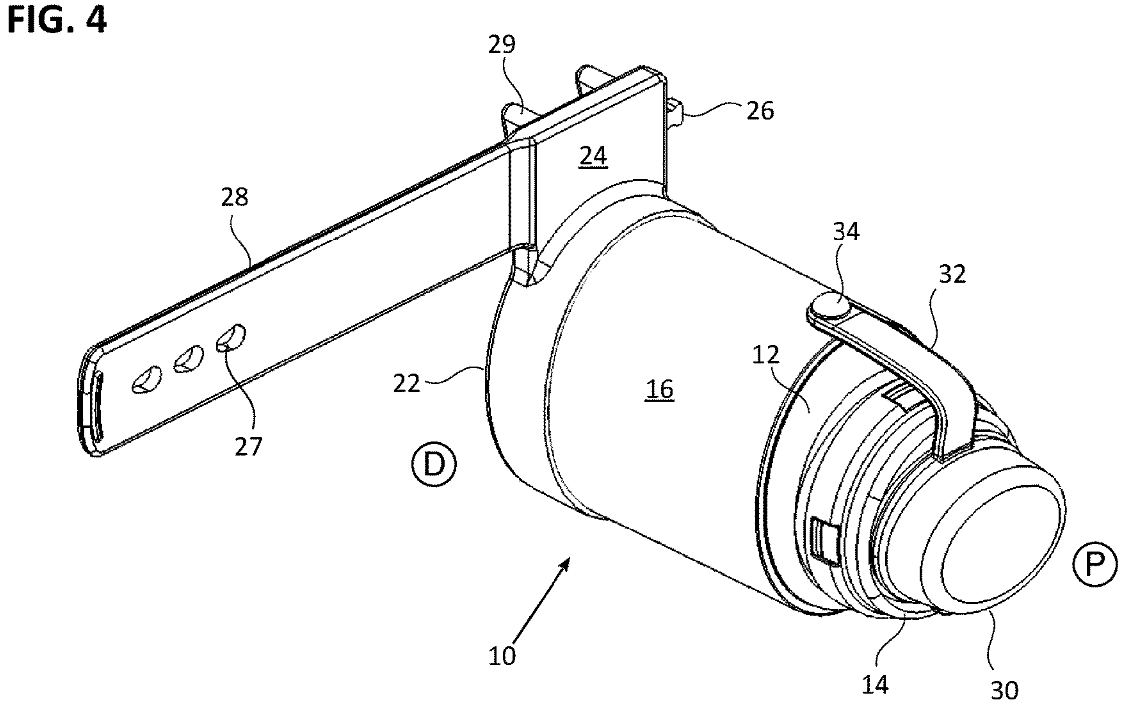

FIGS. 3 and 4 show perspective views of an example of a compact spacer device of the present invention. To specify orientation, the distal end is indicated by the reference label "D" and the proximal end is indicated by the reference label "P". As shown in FIG. 3, the spacer device comprises an aerosol chamber that holds the aerosolized medication from the MDI (not shown). Shown here is the aerosol chamber in extended configuration. The aerosol chamber comprises a fixed barrel 10 and a sliding barrel 12. In this extended configuration, the sliding barrel 12 is telescoped out of the fixed barrel 10. The fixed barrel 10 comprises an outer shell 16 and an inner shell (not shown here). There is an alleyway space between the outer shell 16 and the inner shell of the fixed barrel 10. See also the spacer mouthpiece 14 for insertion into the user's mouth.

At its distal end, the spacer device further comprises an MDI adapter 20 designed to hold the MDI (not shown here) to the aerosol chamber of the spacer device. The MDI adapter 20 is a single piece that has several parts, including an adapter ring 22, a strap mount 24, a strap hook 26, an MDI strap 28, strap holes 27, and cushion bumpers 29. The adapter ring 22 is fitted onto the distal end of the fixed barrel 10. This fastens the MDI adapter 20 to the aerosol chamber. Strap mount 24 protrudes upward from the adapter ring 22. MDI strap 28 extends laterally from strap mount 24. In use, the MDI (not shown) is secured to the MDI adapter 20 by MDI strap 28. The MDI (not shown) is inserted into a rear opening of the MDI adapter 20 that is designed to receive and fit snugly around the mouthpiece of the MDI. The MDI adapter 20 is made of soft plastic (e.g. silicone) to promote a snug fit around the mouthpiece of the MDI. To secure the MDI to the MDI adapter 20, the MDI strap 28 is wrapped around the MDI and hooked onto strap hook 26 at one of the several strap holes 27. By this fastening mechanism, the MDI is pressed against the cushion bumpers 29, which may be useful to dampen loose rattling of the MDI.

FIG. 4 shows the spacer device with the sliding barrel 12 retracted into the fixed barrel 10. This is the spacer device in compact configuration. The sliding barrel 12 slides in the alleyway between the outer shell 16 and inner shell (not shown here) of the fixed barrel 10. Also see the mouthpiece cap 30 that fits over mouthpiece 14. The mouthpiece cap 30 is kept tethered to the main body of the spacer device by a tether 32 that dangles from tether hook 34. The tether 32 is appropriately sized to keep the mouthpiece cap 30 in place, i.e. not too long. In some embodiments, spacer mouthpiece 14 has an antimicrobial coating (e.g. silver ions); and in some cases, whereas spacer mouthpiece 14 has an antimicrobial coating, the outer surface of sliding barrel 12 or the outer surface of outer shell 16 does not have an antimicrobial coating. An outer coating for sliding barrel 12 may be unnecessary because the double-wall design of fixed barrel 10 could work to isolate contaminants on sliding barrel 12. See FIGS. 14A-14D below for more details. In some embodiments, the inside of mouthpiece cap 30 has an antimicrobial coating.

FIGS. 5A and 5B show cross-section cutaway views of the spacer device from alternate perspectives. This cross-section view shows the inner shell 40 of the fixed barrel 10 in relation to the outer shell 16. The outer shell 16 and inner shell 40 are fitted together by a snap ring 46 that joins the two shells at their distal edges. See the narrow alleyway 50 between the inner shell 40 and outer shell 16 of the fixed barrel 10. This narrow alleyway 50 is the space into which the sliding barrel 12 slides in and out of the fixed barrel 10, i.e. allowing telescoping of the sliding barrel 12.

There is a one-way check valve 42 that allows the user to inhale the aerosolized medication in the aerosol chamber. But in case the user exhales, the one-way valve 42 diverts the exhaled breath outward rather than entering the aerosol chamber. See also MDI opening 48 that receives the mouthpiece of the MDI. See also a vent hole 44 that allows necessary airflow when the patient inhales the aerosolized medication. The vent hole 44 is covered with a free swinging vent flap to prevent debris intrusion into the aerosol chamber. This vent flap is designed to swing inward into the aerosol chamber, but not outward.

FIG. 6 shows how the user combines the MDI 60 with the compact spacer device so that they are coupled together. The MDI 60 comprises an actuator 64 that holds the drug aerosol canister 62. The mouthpiece (not shown here) of the actuator 64 is inserted into MDI opening 48 of the spacer device. To properly secure the MDI 60 to the spacer device, the strap 28 is wrapped around the MDI 60 and hooked onto the strap hook 26. The user removes the mouthpiece cap 30 to expose the spacer device mouthpiece 14 and to free the sliding barrel 12. The user then pulls sliding barrel 12 out of fixed barrel 10 to put the spacer device in extended configuration with a larger aerosol chamber.

The user then inserts the spacer device mouthpiece 14 into the user's mouth for inhaling the aerosolized medication. After finishing treatment, the user collapses the spacer device by pushing sliding barrel 12 back into fixed barrel 10, and then puts the mouthpiece cap 30 back onto spacer device mouthpiece 14.

FIGS. 7-12 show perspective views of various parts of the spacer device in isolation. FIG. 7 shows the back side of the MDI adapter 20. See also in this view MDI opening 48 that receives the mouthpiece of the MDI 60 (not shown here) and vent hole 44 to avoid excess negative pressure that could make inhalation more difficult for the user. With the strap 28 tightened around it, the MDI 60 is securely pressed against the cushion bumpers 29, which may be useful to dampen loose rattling of the MDI 60. FIG. 8 shows a rigid subframe 27 that is inserted within the softer MDI adapter 20 to give more rigidity to the adapter ring 22 and strap mount 24 portions.

Figure 9:
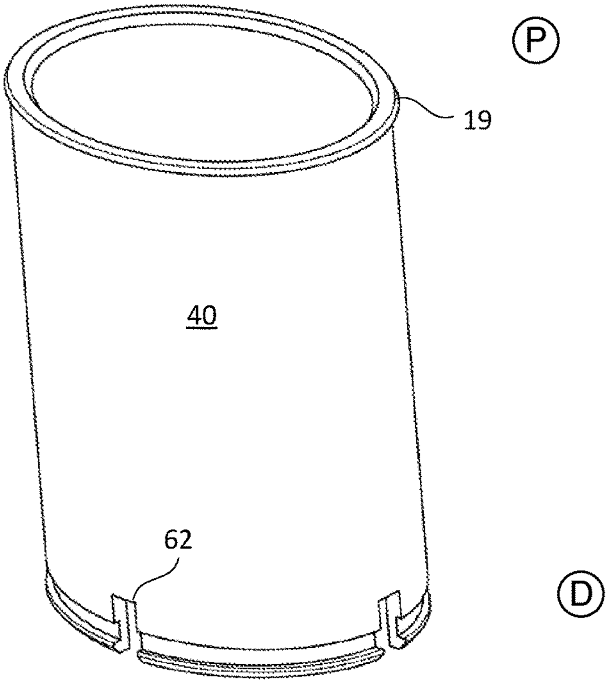
FIG. 9 shows the inner shell of the fixed barrel.
Figure 10:
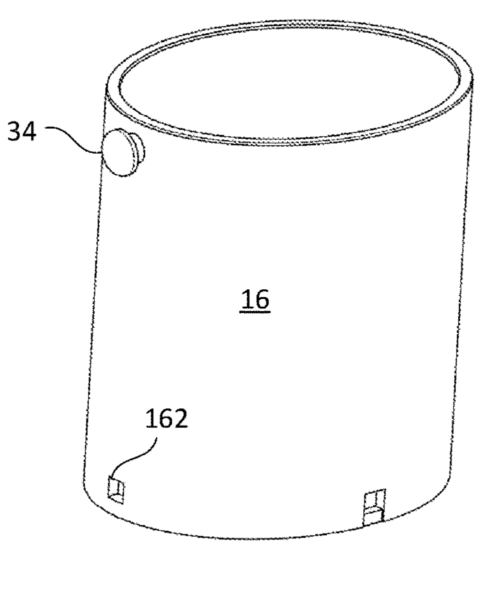
FIG. 10 shows the outer shell of the fixed barrel.
Figure 11:
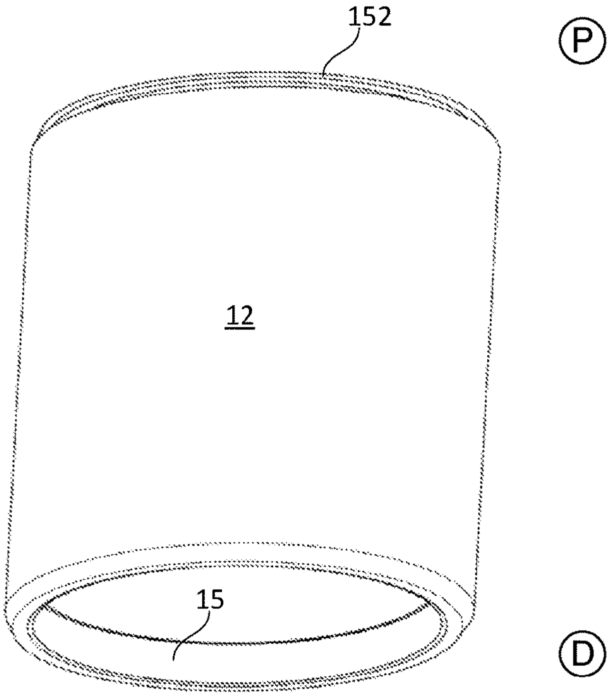
FIG. 11 shows the sliding barrel.
Figure 12:
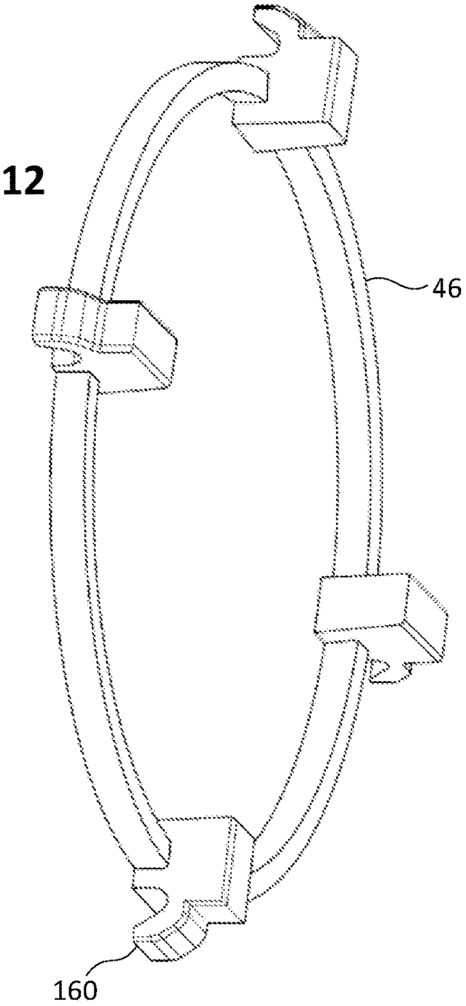
FIG. 12 shows the snap ring that joins the outer shell and the inner shell of the fixed barrel at their distal edges.

FIG. 9 shows the inner shell 40 of the fixed barrel 10. There are notches 62 to fit onto the snap ring 46 (see FIG. 12). There is also a lip 19 at the proximal end of inner shell 40, as further explained below. The length of inner shell 40 is about 6.1 cm. FIG. 10 shows the outer shell 16 of the fixed barrel 10. See catch slots 162 for receiving catch fingers 160 of snap ring 46 (see FIG. 12). FIG. 11 shows the sliding barrel 12 with its spur 152 that snaps onto the valve cap and footpad 15 (see explanation below). As seen in FIGS. 9-11, the fixed barrel 10 and the sliding barrel 12 have an oval shape on transverse cross-section. This is to prevent relative rotation between the two barrels, which would misalign the spacer mouthpiece 14. With the oval shape, the long axis diameter of the inner shell 40 is about 4.1 cm and the short axis diameter is about 3.1 cm. FIG. 12 shows the snap ring 46 that joins outer shell 16 and inner shell 40 at their distal edges. The catch fingers 160 catch onto the catch slots 162 of outer shell 16 (see FIG. 10).

Figure 13A:
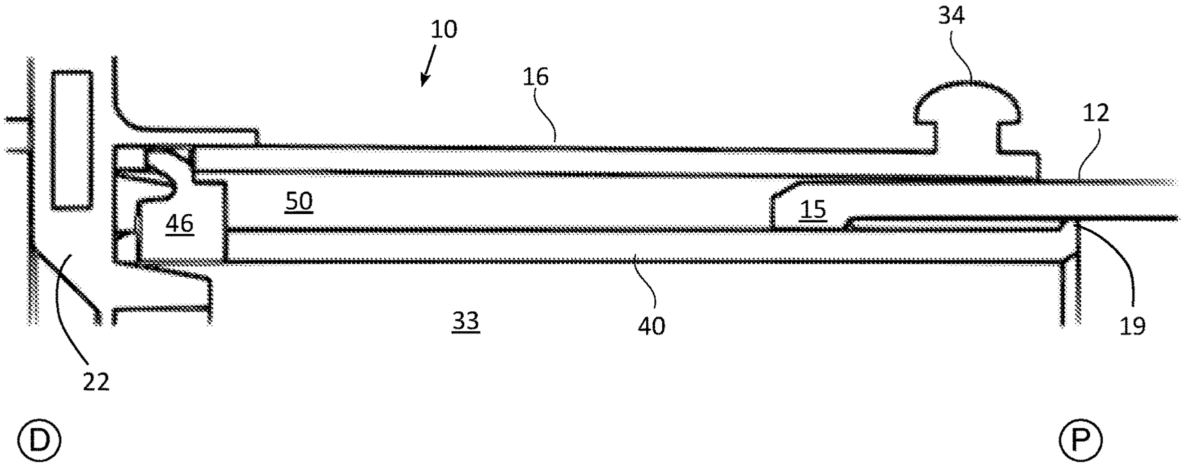
FIGS. 13A-13C show longitudinal cross-section side views of the double-wall design of the fixed barrel.
Figure 13B:
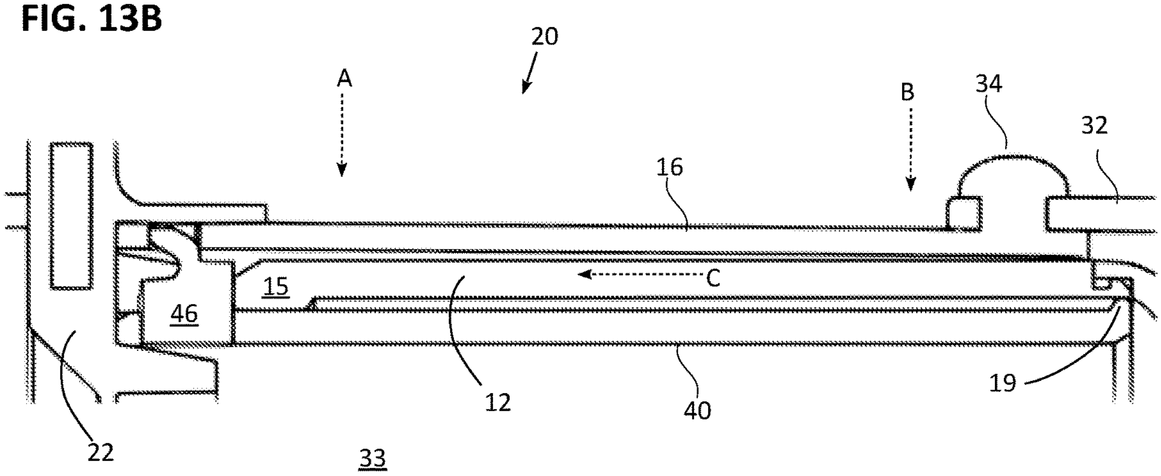

FIGS. 13A and 13B show longitudinal cross-section side views of the double-wall design of the aerosol chamber. The fixed barrel 10 comprises the outer shell 16 and inner shell 40 that are joined by a snap ring 46 that joins the two shells at their distal edges. See also the adapter ring 22 of the MDI adapter 20 that covers the snap ring 46. Between the outer shell 16 and inner shell 40 is a narrow alleyway 50 for holding the sliding barrel 12. The aerosol chamber has an interior space 33.

In FIG. 13A, the sliding barrel 12 is partially pulled out from the double-wall of fixed barrel 10. There is a lip 19 at the proximal end of the inner barrel 40 that protrudes towards the inside of sliding barrel 12 and a footpad 15 at the distal end of sliding barrel 12. This lip 19 helps to create a seal to keep alleyway 50 free of contaminants. The footpad 15 at the distal end of sliding barrel 12 lifts sliding barrel 12 outward (upward in this view) so that the outer (upper) side of sliding barrel 12 seals against the outer shell 16 of the fixed barrel 10. See description of FIG. 19 below for more detail about this outer seal. The footpad 15 also acts as a stop block against overextension of the sliding barrel 12 because it catches on the lip 19 of inner shell 40.

FIG. 13B shows the sliding barrel 12 fully collapsed into the double-wall of fixed barrel 10 by sliding in the direction of arrow C (i.e. putting the spacer device in compact configuration). See tether 32 attached to tether hook 34 to keep the spacer device in compact configuration. As seen here, outer shell 16 has a slight inclined angle relative to inner shell 40. Outer shell 16 also has a slight inclined angle relative to sliding barrel 12. However, sliding barrel 12 and inner shell 40 are parallel to each other. That is, sliding barrel 12 and inner shell 40 have no angle and no incline relative to each other.

The inner shell 40 of fixed barrel 10 and the sliding barrel 12 are mold-constructed with no draft angle. This makes the manufacturing process more difficult, but results in providing a better sealing engagement. Because sliding tube 12 has uniform thickness, its outer surface is in continuous contact with the outer shell 40 to provide a sealing edge at all telescoping positions. For the purpose of defining this zero draft angle feature in numeric terms, on the inner shell 40 of the fixed barrel 10, there is a point A and point B that are separated by a distance of 3 cm. The thickness of the inner shell 40 at point A and point B are essentially the same. Likewise, on sliding barrel 12, there is a point A and point B that are separated by a distance of 3 cm. The thickness of sliding barrel 12 at point A and point B are essentially the same.

Figure 13C:
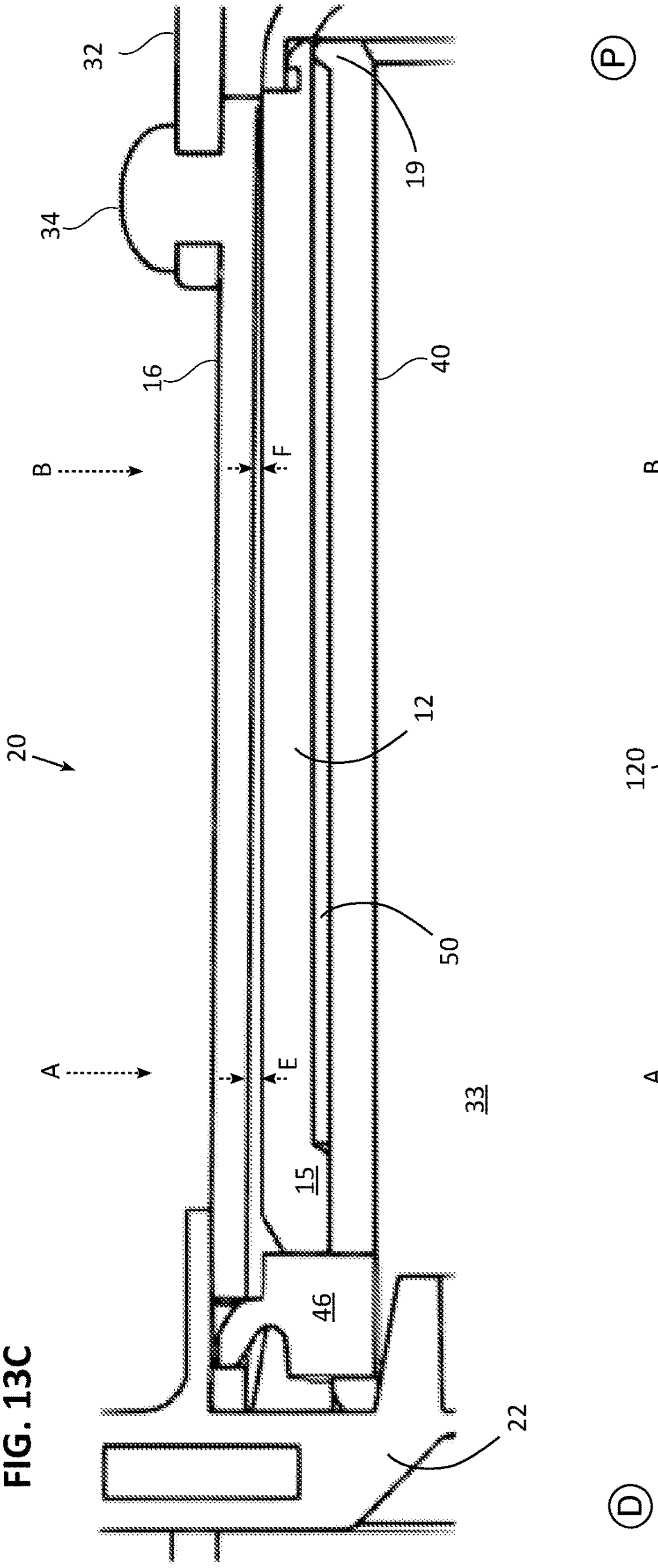

FIG. 13C shows a larger view of the double-wall configuration shown in FIG. 13B to better demonstrate the inclined angle of sliding barrel 12. This inclined angle results in a difference in the gap space between the inner surface of outer shell 16 and the outer surface of sliding barrel 12, i.e. outer gap space. For the purpose of defining this difference in the outer gap space, again consider point A and point B that are separated by a distance of 3 cm. The outer gap space E at point A is wider than the outer gap space F at point B. FIG. 13C also shows that the width of the alleyway 50 between the outer surface of inner shell 40 and the inner surface of outer shell 16 remains constant. This feature is explained in more detail in FIG. 15 below.

Figure 15:
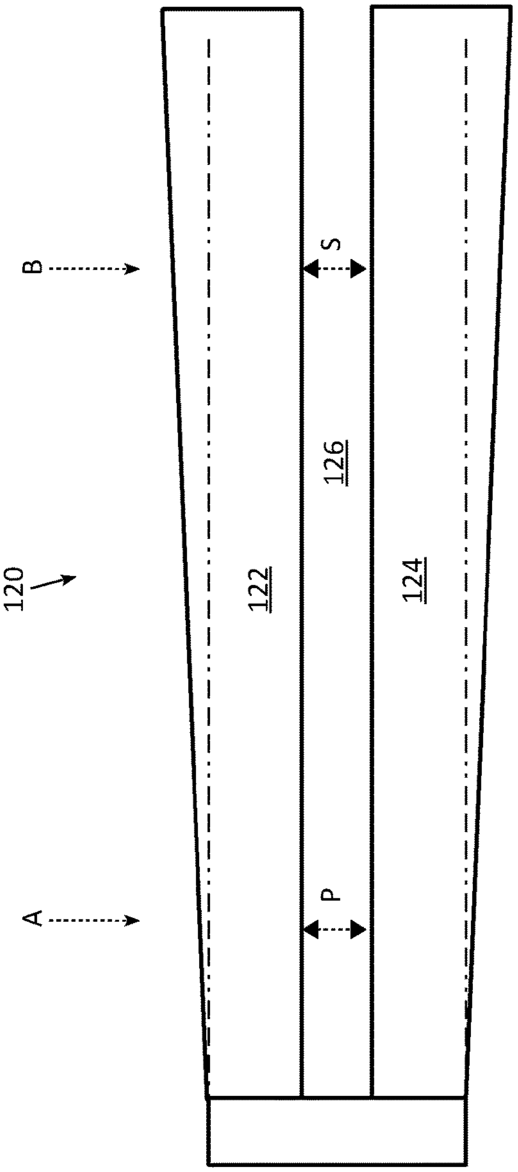
FIG. 15 shows in isolated view, an example of a double-wall portion of a fixed barrel.

The inner and outer shells do not have to be constructed with zero draft on all sides to achieve a constant-width alleyway between the inner and outer shells. FIG. 15 shows in isolated view, an example of a double-wall portion of a fixed barrel. This is a schematic diagram with disproportionate dimensions and exaggerated scaling to better emphasize the features being discussed. See that the fixed barrel 120 has an outer shell 122 and an inner shell 124. Between them is the alleyway 126 into which the sliding barrel (not shown) slides in/out.

The width of this alleyway 126 is constant throughout, except for minor accessory features like ridges or bumps. For the purpose of defining this constant-width feature, again consider point A and point B which are separated by a distance of 3.0 cm. The width P of alleyway 126 at point A is substantially the same as width S at point B. Note that complete zero draft construction is not needed to have this constant-width feature. A disadvantage of zero draft molding is that it makes the manufacturing process more difficult. In particular, note that outer shell 122 has a tapered draft angle on the outside (see compared to dashed line), but zero draft angle for the inside surface. Likewise, inner shell 124 has a tapered draft angle on the outside (see compared to dashed line), but zero draft angle for the inside surface.

Figure 19:
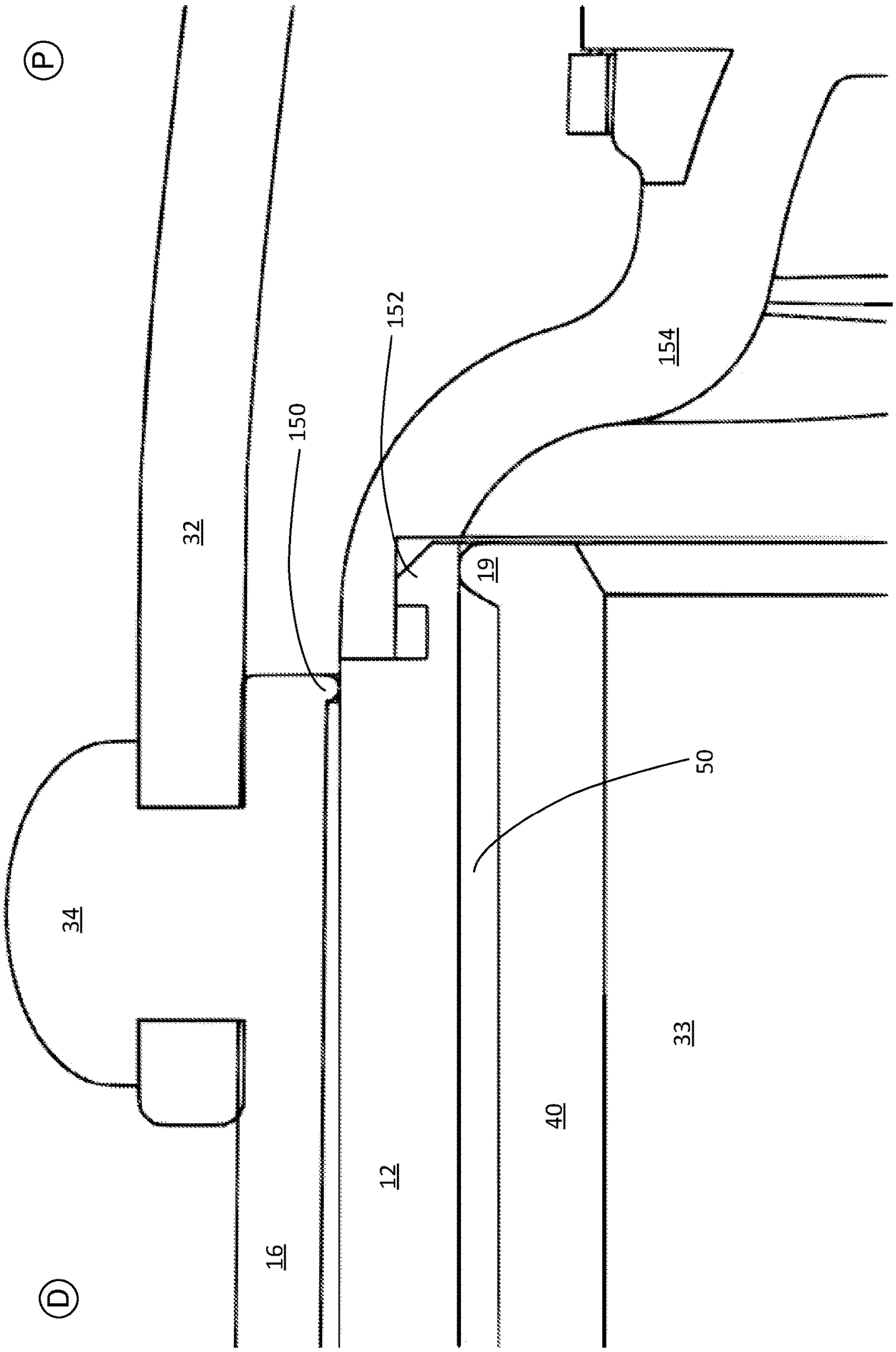
FIG. 19 shows a closeup view of the proximal end of the aerosol chamber for the spacer device depicted in FIGS. 13A-13C.

FIG. 19 shows a closeup enlarged view at the proximal end of the aerosol chamber. This view is near the valve cap 154 for the one-way valve. See outer shell 16, sliding barrel 12, inner shell 40, and interior space 33 of the aerosol chamber as already explained above. Also see tether 32 and tether hook 34. Shown here in better detail is the sealing bump 150 on the inside surface of outer shell 16 and pointing towards the outer surface of sliding barrel 12. This sealing bump 150 maintains continuous contact with the outer surface of sliding barrel 12 as sliding barrel 12 slides in and out. Also shown in more detail is lip 19 that maintains continuous contact with the inner surface of sliding barrel 12 as sliding barrel 12 slides in and out. Together, lip 19 and sealing bump 150 work to form a seal that keeps alleyway 50 free of outside contaminants. Also shown in more detail is the spur 152 on sliding barrel 12 that snaps into the valve cap 154.

Figure 14A:
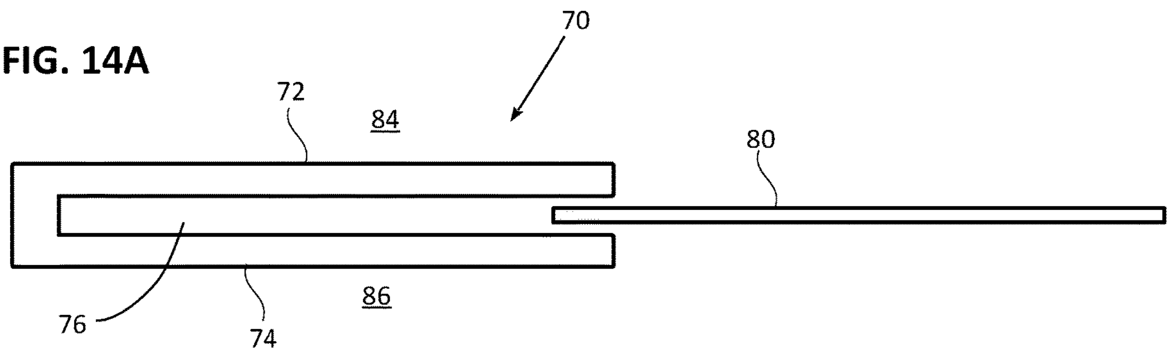
FIGS. 14A-14D show how contaminants are kept away from the interior of the aerosol chamber.
Figure 14B:
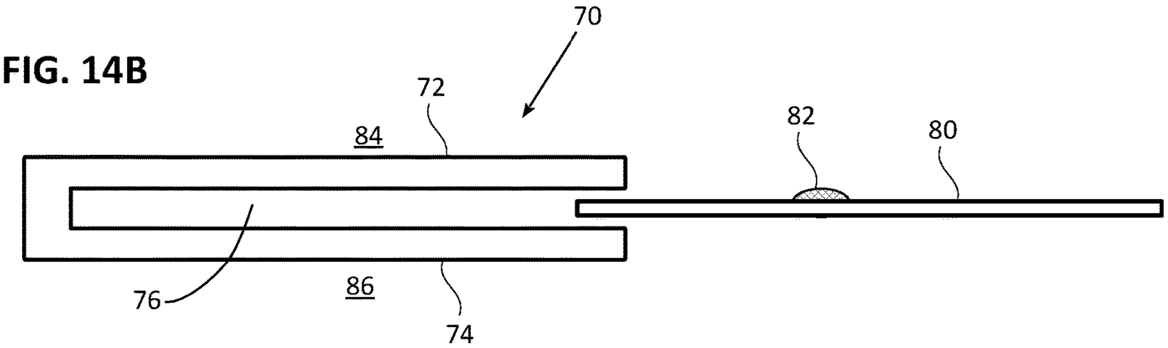
Figure 14C:
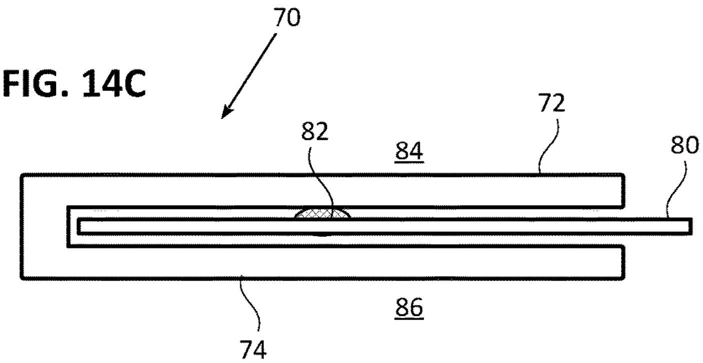
Figure 14D:
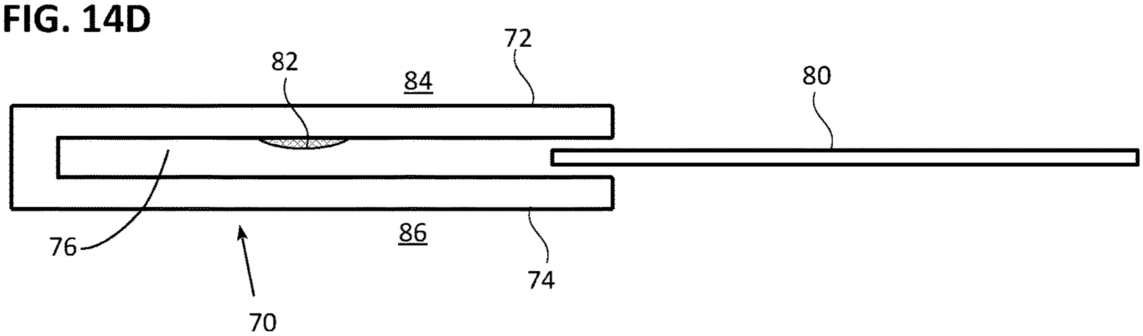

FIGS. 14A-14D show how contaminants are kept away from the interior of the aerosol chamber. Shown here is a schematic representation of the double-wall design of the aerosol chamber in cross-section view with the external side 84 and interior space 86 of the aerosol chamber. The double-wall of the fixed barrel 70 is an outer shell 72 and an inner shell 74. In FIG. 14A, the sliding barrel 80 is in extended configuration for operational use. FIG. 14B shows a contaminant 82 (e.g. dirt or oil from fingertips, aerosol droplet, viruses, bacteria, etc.) that lands on the exterior surface of sliding barrel 80. After finished with the treatment, the user pushes sliding barrel 80 into the fixed barrel 70 so that the spacer device is put into compact configuration. As shown in FIG. 14C, the contaminant 82 gets smeared onto the inside surface of the outer shell 72. Note that the interior space 86 of the aerosol chamber is not exposed to the contaminant 82. As shown in FIG. 14D, when the spacer device is used again and the user pulls out the sliding barrel 80, the contaminant 82 remains in the alleyway 76 between the double-walls. Thus, the contaminant 82 is confined to the alleyway 76 in the double-wall. There could also be residue of the contaminant 82 on the outer surface of sliding barrel 80. But in any case, the interior space 86 of the aerosol chamber is kept from exposure to the contaminant 82.

Figure 16A:
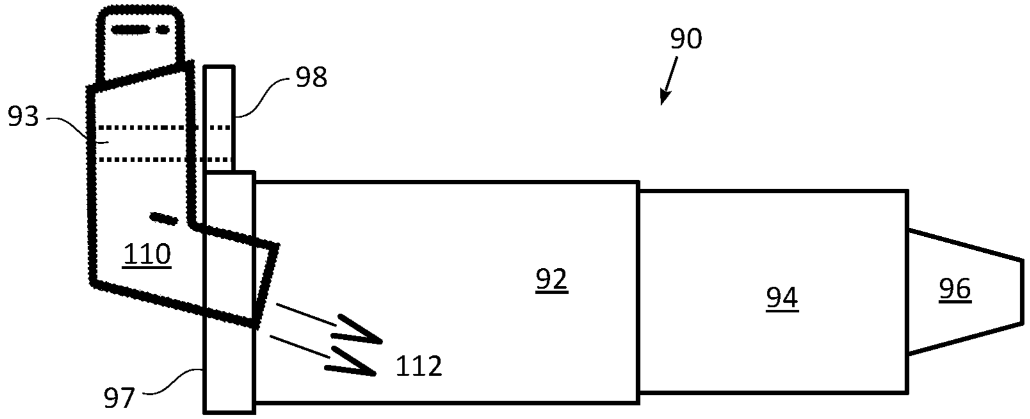
FIG. 16A shows an example of a spacer device without a cushion bumper.
Figure 16B:
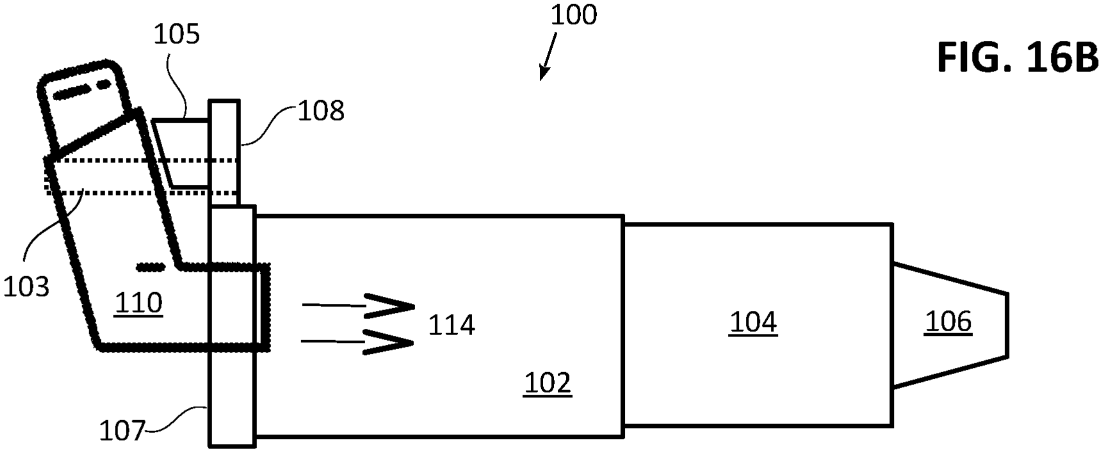
FIG. 16B shows an example of a spacer device with cushion bumper.
Figure 16C:
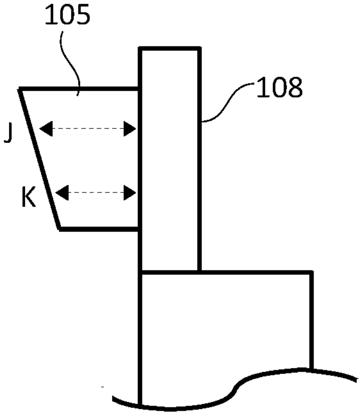
FIG. 16C shows a close-up view of the cushion bumper.

FIGS. 16A-16C show how the cushion bumper on the MDI adapter could be particularly useful. Most MDI devices are designed with an inclined angle between the boot and the spray outlet/mouthpiece. This shape facilitates handling by the user when the MDI is being used directly (without a spacer). However, this inclined configuration could present a problem when used with a spacer. This is demonstrated in FIG. 16A, which shows an example of our spacer device 90 without a bumper on the MDI adapter 97. See that spacer device 90 comprises a fixed barrel 92, sliding barrel 94 in extended configuration, and mouthpiece 96. The MDI adapter 97 has a strap mount 98, but does not have a bumper. Meanwhile, the MDI 110 is strapped in by strap 93 (shown in dotted line for clarity of illustration) so that the boot of the MDI 110 is pressed flush against strap mount 98. The problem is that this fitting points the spray outlet of the MDI 110 in a downward, off-center direction. This directs the spray plume 112 downwards towards the wall of the aerosol chamber.

See now FIG. 16B, which shows an example of an alternate design of our spacer device with a cushion bumper. Here, spacer device 100 comprises a fixed barrel 102, sliding barrel 104 in extended configuration, and mouthpiece 106. The MDI adapter 107 has a strap mount 108 that has a cushion bumper 105 on its back side. Meanwhile, the MDI 110 is strapped in by strap 103 (shown in dotted line for clarity of illustration) so that the boot of the MDI 110 is pressed in towards strap mount 108, but stopped by cushion bumper 105 so that MDI 110 is positioned at its natural inclined angle. This fitting correctly points the spray outlet of the MDI in a straight direction. This directs the spray plume 114 towards the center of the aerosol chamber, where it is most effective.

FIG. 16C shows a close-up view of the cushion bumper 105 in isolation. See that cushion bumper 105 has an inclined angle that conforms to the incline angle of the MDI. For the purpose of defining this inclined angle feature of bumper 105, consider point J and point K which are separated by a distance of 0.75 cm. Point K is located closer to the central longitudinal axis of the spacer device than point J. At each point, the double arrow shows the elevation of bumper 105 relative to strap mount 108. See that the elevation at point J is higher than the elevation at point K, i.e. because of the inclined angle.

Figure 17A:
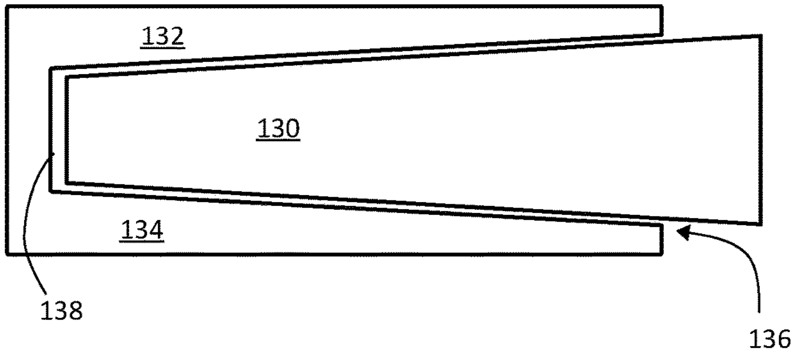
FIGS. 17A and 17B show cross-section side views of an aerosol chamber in isolation.
Figure 17B:
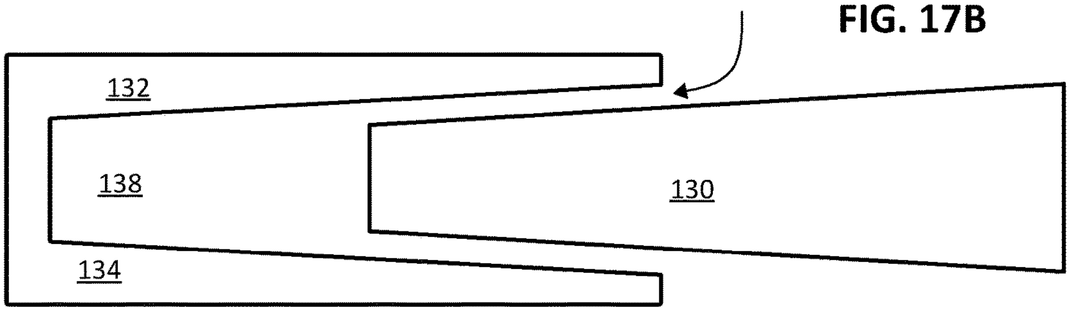
Figure 18A:
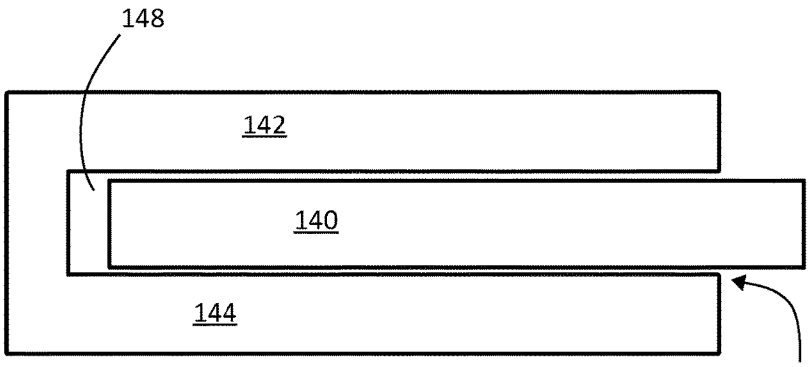
FIGS. 18A and 18B show cross-section side views of a different aerosol chamber in isolation.
Figure 18B:
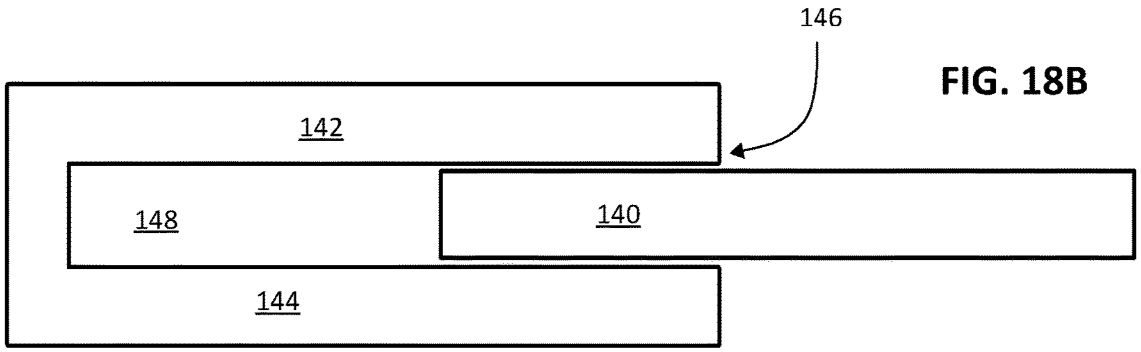

A comparison of FIGS. 17A and 17B against FIGS. 18A and 18B show how having a constant-width alleyway can be useful for improved sealing of the aerosol chamber. These are schematic diagrams with disproportionate dimensions and exaggerated scaling to better emphasize the features being discussed. FIG. 17A shows an example of an aerosol chamber design that gives inconsistent sealing. The fixed barrel comprises outer shell 132 and inner shell 134 with an alleyway 138 therebetween. Both outer shell 132 and inner shell 134 have draft angles on the inside such that the width of alleyway 138 is not constant-width throughout. The sliding barrel 130 conforms to this non-rectangular shape. There is a slight gap 136 around sliding barrel 130 which represents an inherently imperfect mechanical seal.

Now see FIG. 17B in which sliding barrel 130 is halfway withdrawn from the fixed barrel. Notice that sealing gap 136 has substantially enlarged. This happens because the alleyway 138 and the wall of sliding barrel 130 are not perfectly rectangular shaped.

Compare this with FIG. 18A which shows an example of an aerosol chamber design that gives more consistent sealing. The fixed barrel comprises outer shell 142 and inner shell 144 with an alleyway 148 therebetween. Both outer shell 142 and inner shell 144 have no draft angles on the inside such that the width of alleyway 148 is constant throughout. The sliding barrel 140 conforms to this perfectly rectangular shape. There is a slight gap 146 around sliding barrel 140 which represents an inherently imperfect mechanical seal. Now see FIG. 18B in which sliding barrel 140 is halfway withdrawn from the fixed barrel. Unlike the above design, notice that sealing gap 146 does not enlarge.

This happens because the alleyway 148 and the wall of sliding barrel 140 have a perfectly aligned rectangular shape.

Experimental Work

Three prototypes of the device were made and benchtop testing performed in comparison against a comparable predicate spacer device. The following aerosol tests were performed by conventional cascade impactor techniques using a solution of albuterol sulfate as the test drug. The following parameters were measured for the amount of drug expelled by the spacer devices: total drug amount expelled, total respirable drug amount expelled, coarse drug particle amount, fine drug particle amount, and ultra-fine drug particle amount. In comparison to the predicate spacer device, the prototype devices expelled (per burst) 11% more total drug dose amount, 4% more total respirable drug dose amount, 32% more coarse particle amount, 10% more fine particle amount, and 61% more ultra-fine particle amount. Thus, by all parameters, the prototype devices outperformed the predicate device.

The descriptions and examples given herein are intended merely to illustrate the invention and are not intended to be limiting. Each of the disclosed aspects and embodiments of the invention may be considered individually or in combination with other aspects, embodiments, and variations of the invention. In addition, unless otherwise specified, the steps of the methods of the invention are not confined to any particular order of performance. Modifications of the disclosed embodiments incorporating the spirit and substance of the invention may occur to persons skilled in the art, and such modifications are within the scope of the invention.

Any use of the word "or" herein is intended to be inclusive and is equivalent to the expression "and/or," unless the context clearly dictates otherwise. As such, for example, the expression "A or B" means A, or B, or both A and B. Similarly, for example, the expression "A, B, or C" means A, or B, or C, or any combination thereof.

We claim:

1. A spacer device for a metered dose inhaler (MDI), comprising:
- a fixed barrel comprising an inner shell, an outer shell spaced radially outward from the inner shell, and an annular alleyway formed therebetween;
- the inner shell having an outer surface and an inner surface;
- a sliding barrel in telescoping engagement with the fixed barrel, wherein the sliding barrel is configured to slide within the alleyway between the inner shell and outer shell of the fixed barrel;
- the sliding barrel having an outer surface and an inner surface;
- wherein the fixed barrel and the sliding barrel together form an aerosol chamber that has a proximal end and a distal end;
- at the distal end of the aerosol chamber, an MDI adapter that has an opening to receive a spray outlet of an MDI and a fastening mechanism to secure the MDI to the spacer device;
- a mouthpiece at the proximal end of the aerosol chamber.

2. The spacer device of claim 1, wherein the fastening mechanism on the MDI adapter comprises a strap mount and a strap extending from the strap mount.

3. The spacer device of claim 2, wherein the strap mount on the MDI adapter has a bumper on a side facing the MDI.

4. The spacer device of claim 3, wherein the spacer device has a central longitudinal axis, and wherein an elevation of the bumper relative to the strap mount decreases along a direction towards the central longitudinal axis of the spacer device.

5. The spacer device of claim 1, wherein the MDI adapter comprises a material that is softer and more flexible than the fixed barrel and the sliding barrel.

6. The spacer device of claim 1, wherein two points separated by a distance of 3.0 cm, point A and point B, are defined on the fixed barrel; and wherein the width of the alleyway at point B differs from the width at point A by an amount that is less than 8% of the width at point A.

7. The spacer device of claim 6, wherein the width of the alleyway at point A and point B is the same at both points.

8. The spacer device of claim 6, wherein the thickness of both the inner shell and the outer shell at points A and point B are different.

9. The spacer device of claim 1, wherein two points separated by a distance of 3.0 cm, point A and point B, are defined on the fixed barrel; wherein the thickness of the inner shell at point B differs from the thickness at point A by an amount that is less than 8% of the thickness at point A.

10. The spacer device of claim 1, wherein two points separated by a distance of 3.0 cm, point A' and point B', are defined on the sliding barrel, wherein the thickness of the sliding barrel at point B' differs from the thickness at point A' by an amount that is less than 8% of the thickness at point A'.

11. The spacer device of claim 10, wherein the thickness of the sliding barrel at point B' is the same as the thickness at point A'.

12. The spacer device of claim 1, wherein two points separated by a distance of 3.0 cm, point A and point B, are defined on the aerosol chamber in compact configuration such that point A is distal to point B;
- wherein an outer gap is the width of the gap between the inner surface of the outer shell and the outer surface of the sliding barrel;
- wherein the outer gap at point A is wider than the outer gap at point B.

13. The spacer device of claim 12, wherein the outer gap at point A is at least 25% wider than the outer gap at point B.

14. The spacer device of claim 1, wherein the spacer device further comprises a one-way valve.

15. The spacer device of claim 1, wherein the MDI adapter comprises a vent hole covered with a flap.

16. A method of using a metered dose inhaler with the spacer device, comprising:
- having the spacer device of claim 1;
- having a metered dose inhaler (MDI) comprising a spray outlet;
- inserting the spray outlet of the MDI into the opening of the MDI adapter;
- securing the MDI to the spacer device with the fastening mechanism;
- pulling the sliding barrel out of the fixed barrel to put the aerosol chamber in extended configuration;
- using the MDI for treatment;
- pushing the sliding barrel back into the fixed barrel to put the aerosol chamber in compact configuration.

17. The method of claim 16, wherein the fastening mechanism on the MDI adapter comprises a strap mount and a strap extending from the strap mount; and
- wherein the step of securing the MDI to the spacer device comprises wrapping the strap around the MDI to secure the MDI to the spacer device.

18. The method of claim 16, wherein the spacer device further comprises a mouthpiece cap and a tether that is connected to both the mouthpiece cap and the aerosol chamber; wherein the mouthpiece cap covers the mouthpiece; and the method further comprises removing the mouthpiece cap to expose the mouthpiece and free the sliding barrel from restraint by the tether.

19. The method of claim 18, further comprising putting the mouthpiece cap back onto the spacer device mouthpiece.

20. The method of claim 16, wherein a contaminant touches on the sliding barrel while it is pulled out of the fixed barrel;

wherein the inside of the aerosol chamber is not exposed to the contaminant when the sliding barrel is pushed back into fixed barrel;

wherein the inside of the aerosol chamber is not exposed to the contaminant when the sliding barrel is then again pulled out of the fixed barrel.

* * * * *